United States Patent [19]

Takubo et al.

[11] Patent Number: 5,659,093
[45] Date of Patent: Aug. 19, 1997

[54] METHOD OF PRODUCING 1,1,1,3,3-PENTAFLUOROPROPANE, A METHOD OF PRODUCING 1,1,1,3,3-PENTAFLUORO-2-HALOGENO-3-CHLOROPROPANE, AND A METHOD OF PRODUCING 1,1,1,2,3,3-HEXACHLOROPROPENE

[75] Inventors: Seiji Takubo; Hirokazu Aoyama; Tatsuo Nakada, all of Settsu, Japan

[73] Assignee: Daikin Industries Ltd., Osaka, Japan

[21] Appl. No.: 464,834

[22] PCT Filed: Dec. 24, 1993

[86] PCT No.: PCT/JP93/01887

§ 371 Date: Jun. 27, 1995

§ 102(e) Date: Jun. 27, 1995

[87] PCT Pub. No.: WO94/14736

PCT Pub. Date: Jul. 7, 1994

[30] Foreign Application Priority Data

Jun. 10, 1992 [JP] Japan ................ 5-165229
Dec. 29, 1992 [JP] Japan ................ 4-360964
Dec. 29, 1992 [JP] Japan ................ 4-360965

[51] Int. Cl.$^6$ ............................................. C07C 19/08
[52] U.S. Cl. ...................... 570/167; 570/176; 570/229
[58] Field of Search ........................ 570/167, 176, 570/229

[56] References Cited

U.S. PATENT DOCUMENTS

| 2,637,747 | 5/1953 | McBee | 570/167 |
| 2,724,004 | 11/1955 | Frederick | 570/167 |
| 2,942,036 | 6/1960 | Smith et al. | 570/176 |
| 3,639,493 | 2/1972 | Campbell | 570/229 |
| 4,980,324 | 12/1990 | Kellner et al. | 570/176 |
| 5,447,896 | 9/1995 | Rao | 570/176 |

FOREIGN PATENT DOCUMENTS

| 0347830 | 12/1989 | European Pat. Off. | 570/176 |
| 63-5037 | 1/1988 | Japan | 570/229 |

*Primary Examiner*—C. Warren Ivy
*Assistant Examiner*—Lyman H. Smith
*Attorney, Agent, or Firm*—Armstrong, Westerman, Hattori, McLeland & Naughton

[57] ABSTRACT

There are provided production methods of 1,1,1,3,3-pentafluoropropane characterized in that 1,1,1,3,3-pentafluoro-2,3-dichloropropane is reacted with hydrogen fluoride in the presence of a noble metal catalyst; of 1,1,1,3,3-pentafluoro-2-halogeno-3-chloropropane characterized in that the halogenated propene indicated as general formula I is fluorinated in the presence of antimony trihalogenide and/or antimony pentahalogenide by hydrogen fluoride of mole ratio of or over five times the said antimony halogenide in a liquid phase; and of 1,1,1,2,3,3-hexaohloropropene characterized in that 1,1,1,2,2,3,3-heptachloropropane is reacted with an aqueous solution of alkali metal hydroxide in the presence of a phase transfer catalyst. Therefore, an industrial manufacturing method which is possible to obtain the objective product easily at low cost and high yield can be provided.

10 Claims, No Drawings

METHOD OF PRODUCING 1,1,1,3,3-PENTAFLUOROPROPANE, A METHOD OF PRODUCING 1,1,1,3,3-PENTAFLUORO-2-HALOGENO-3-CHLOROPROPANE, AND A METHOD OF PRODUCING 1,1,1,2,3,3-HEXACHLOROPROPENE

This application is a 35 U.S.C. 371 national stage filing of PCT/JP93/0188 published as WO 94/14736 on Jul. 7, 1994.

1. Industrial fields where the invention can be utilized

This invention relates to a method of producing 1,1,1,3,3-pentafluoropropane which is a useful compound usable as a substitute for CFC and HCFC which are utilized for a cooling medium, a blowing agent or a cleaning agent and is particularly useful as a urethane blowing agent, besides, a method of producing 1,1,1,3,3-pentafluoro-2-halogeno-3-chloropropane which can be a synthetic intermediate of 1,1,1,3,3-pentafluoropropane, and a method of producing 1,1,1,2,3,3-hexachloropropene.

2. Prior art

As a method of preparing 1,1,1,3,3-pentafluoropropane, a reductive reaction with hydrogen wherein 1,2,2-trichloropentafluoropropane is used as a raw material is known (U.S. Pat. No. 2,942,036).

However, this reaction is not suitable for industrial use due to low yield and generation of 2-chloropentafluoropropene and 1,1,3,3,3-pentafluoropropene which are not reduced enough.

On the other hand, 1,1,1,3,3-pentafluoro-2-halogeno-3-chloropropane is useful by itself as an intermediate of medicines or agricultural chemicals and is a useful compound for the industrial use which can be conducted to hydrofluorocarbon as a substitute for HCFC and CFC which are used as various cooling mediums, blowing agents or cleaning agents, by fluorination or reduction and which can be conducted to monomers of various kinds of resins by dehydrochlorination. Especially, 3,1,1,3,3-pentafluoro-2,3-dichloropropane can be useful as a raw material of 1,1,1,3,3-pentafluoropropane.

Until now, a method of fluorinating propene halogenide with HF in a liquid phase under the presence of a antimony halogenide is known. For example, E. T. McBee et al. obtained 1,1,1,3,3-pentafluoro-2,3-dichloropropane by fluorinating 1,1,1-trifluoro-2,3,3-trichloropropene with HF under the presence of antimony catalyst (J. Am. Chem. Soc. 70, 2023, (1948)).

However, because 1,1,1-trifluoro-2,3,3-trichloropropene, HF and antimony catalyst as raw materials are supplied at once to a reactor before reaction, not only this reaction needs high reaction temperature of 250° C., but also the yield of 1,1,1,3,3-pentafluoro-2,3-dichloropropane is so low as to be 50%, thus this reaction cannot be used industrially.

Besides, 1,1,1,2,3,3-hexaohloropropene is useful as an intermediate of various medicines or agricultural chemicals and is a useful raw material by which an intermediate of various fluorine compounds can be synthesized by fluorinating chlorine of this propene with HF. Especially, it is useful as a raw material of 1,1,1,3,3-pentafluoro-2,3-dichloropropane (HCFC 225da).

Generally, 1,1,1,2,3,3-hexaohloropropene can be synthesized by dehydrochlorination of 1,1,1,2,2,3,3-heptachloropropane. 1,1,1,2,2,3,3-heptachloropropane being a raw material is an economical industrial raw material which can be easily synthesized from chloroform and tetrachloroethylene as economical industrial raw materials.

Hitherto, there is known a method of synthesizing 1,1,1,2,3,3-hexachloropropene by dehydrochlorination of 1,1,1,2,2,3,3-heptachloropropane with alkali metal hydroxide like KOH in alcohol solvent (J. Am. Chem. Soc., 63,1438 (1941)).

However, because of using alcohol as the reaction solvent, this meth6d needs to filtrate the alkali metal chloride produced after the reaction and then separate the product from alcohol by the use of the operation such as distillation.

And, it is also known that by passing through a reaction tube heated around 400° C., it can be obtained from 1,1,1,2,2,3,3-heptachloropropane, but this reaction requires high temperature and use of expensive metal for the material of the reaction tube because of the generation of HCl in the reaction.

OBJECT OF THE INVENTION

The first object of this invention is to provide a method being able to produce 1,1,1,3,3-pentafluoropropane (HFC 245fa) enough in high selectivity in which any problems as mentioned above do not occur.

The second object of this invention is to provide an industrial manufacturing method which can overcome the above-mentioned problems included in the prior art method of producing 1,1,1,3,3-pentafluoro-2-halogeno-3-chloropropane and by which 1,1,1,3,3-pentafluoro-2-halogeno-3-chloropropane (especially, HCFC 225da) can be easily produced at low cost and high yield.

The third object of this invention is to solve the problems included in the above-mentioned prior arts and to provide a method of economically producing 1,1,1,2,3,3-hexachloropropene which can be industrially easily performed.

THE CONSTITUTION OF THE INVENTION

As a result of earger study by the inventors regarding a method of producing 1,1,1,3,3-pentafluoropropane to solve the above-mentioned problems, they found that the objective product can be obtained at high yield when a reductive reaction with hydrogen (catalytic reduction) was performed by the use of 1,1,1,3,3-pentafluoro-2,3-dichloropropane as a raw material under the presence of noble metal catalyst such as palladium in a gaseous phase, having completed the first invention.

That is, the summary of the first invention is resided in a method of producing 1,1,1,3,3-pentafluoropropane at high selectivity of not less than 80% by hydrogen reduction reaction using 1,1,1,3,3-pentafluoro-2,3-dichloropropane as a raw material, in a gaseous phase system in the presence of the noble metal catalyst such as palladium particularly at the temperature from 30° to 450° C.

In the first invention, it is particularly important that the hydrogen reduction is carried out with the noble metal catalyst in a gaseous phase. For the gaseous phase reaction system of the gaseous phase reaction, a fixed bed-type gaseous phase reaction, a fluidized bed-type gaseous phase reaction and so on can be adopted.

As the noble metal of the noble metal catalyst, palladium and platinum and the like can be nominated and from the point of a selectivity of the reaction, that is, from the point of the small amount of by-product palladium is preferable. These are desirably carried on at least one kind of carriers selected from active carbon, silica gel, titanium oxide, zirconia and so on.

Besides, the particle diameter of the carrier does not scarcely affect the reaction, however, it is desirable 0.1 to 100 mm.

And, the carrying concentration can be applied in wide range from 0.05 to 10% (by weight), but it is usually recommended to be from 0.5 to 5%.

The reaction temperature is usually from 30° to 450° C., preferably 70° to 400° C.

In the reductive reaction with hydrogen of 1,1,1,3,3-pentafluoro-2,3-dichloropropane, the ratio of hydrogen to the raw material can be varied widely. But usually, at least a stoichiometric amount of hydrogen is used for the hydrogenation. Hydrogen of rather more than the stoichiometric amount, for example, 8 mole or more 8 mole to the total mole of the starting material can be used.

A reaction pressure is not particularly limited and the reaction can be carried out under pressure, reduced pressure or normal pressure, but preferable under pressure or normal pressure because the equipment is complicated under reduced pressure.

Contact times are usually in the range of 0.1 to 300 seconds, particularly in the range of 1 to 30 seconds.

The raw material, 1,1,1,3,3-pentafluoro-2,3-dichloropropane is a known compound and can be obtained by the reaction of fluorinating 1,1,1-trifluoro-2,3,3-trichloropropene (E. T. McBEE, ANTHONY TRUCHAN and R. O. BOLT, J. Amer. Chem. Soc., vol 70, 2023–2024 (1948)).

Besides, as a result of earger study by the inventors in relation to a method of producing 1,1,1,3,3-pentafluoropropane for solving the above-mentioned problems, they found that the objective product can be obtained at a high yield when a reductive reaction with hydrogen was carried out by the use of 1,1,1,3,3-pentafluoro-2,3-dichloropropane as a raw material in a gaseous phase under the presence of a catalyst in which at least one kind of elements selected from zirconium and vanadium are added to palladium, having completed the second invention.

That is, the summary of the second invention is in a method of producing 1,1,1,3,3-pentafluoropropane at high yield of not less than 80% by the reductive reaction with hydrogen particularly at the temperature from 30° to 450° C. in a gaseous system by the use of 1,1,1,3,3-pentafluoro-2,3-dichloropropane as a raw material in the presence of a catalyst in which at least one kind of elements selected from zirconium and vanadium are added to palladium.

In the second invention, it is particularly important that the hydrogen reduction reaction is carried out in a gaseous phase system particularly with the catalyst of palladium added by at least one kind of elements selected from zirconium and vanadium. For the gaseous phase reaction system, a fixed bed-type paseous phase reaction, a fluidized bed-type gaseous phase reaction and so on can be adopted.

The addition amount of zirconium and/or vanadium to palladium is usually 0.01 to 4, preferably 0.1 to 2 in the mole retio.

The catalyst to which at least one kind of elements selected from zirconium and vanadium are added is desirable to be carried on at least one kind of carriers selected from active carbon, silica gel, titanium oxide, zirconia and so on.

In this case the above-mentioned metal carried thereon can be in the form of salt and nitrate, oxide salt, oxide, chloride and the like can be used.

And the particle diameter of the carrier does not scacely affect the reaction, however, it is desirable 0.1 to 100 mm.

As the carrying concentration, it can be used in the wide range from 0.05 to 10%, but a product with 0.5 to 5% is usually recommended.

The reaction temperature is usually from 30° to 450° C., preferably 70° to 400° C.

In the reductive reaction with hydrogen of 1,1,1,3,3-pentafluoro-2,3-dichloropropane, the ratio of hydrogen to the raw material can be varied widely, But usually, at least a stoichiometric amount of hydrogen is used for the hydrogenation. Hydrogen of rather more than the stoichiometric amount, for example, 8 mole or more 8 mole to the total mole of the starting material can be used.

A reaction pressure is not particularly limited and the reaction can be carried out under pressure, reduced pressure or normal pressure, but preferable under pressure or normal pressure because the equipment is complicated under reduced pressure.

Contact times are usually in the range of 0.1 to 300 seconds, particularly in the range of 1 to 30 seconds.

Besides, to solve the above-mentioned problem, the inventors found s method of producing 1,1,1,3,3-pentafluoro-2-halogeno-3-chloropropane (for example, 1,1,1,3,3-pentafluoro-2,3-dichloropropane) characteried by fluorinating propene halogenide indicated as general formula I:

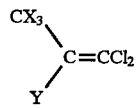

(provided that in this general formula, X and Y are Cl or F respectively.)

(for example, 1,1,1,2,3,3-hexachloropropene) with hydrogen fluoride in the presence of antimony trihalogenide and/or antimony pentahalogenide in a liquid phase, wherein the hydrogen fluoride of mole ratio of or over five times antimony trihalogenide and/or antimony pentahalogenide is present in the reaction system, so that they have reached the third invention.

The third invention is, for example, to produce 1,1,1,3,3-pentafluoro-2-halogeno-3-chloropropane by fluorinating propene halogenide of the above-mentioned general formula I in the coexistence of fluorinated-chlorinated antimony being antimony trihalogenide and HF.

In the third invention, it is known that antimony chloride added to the reaction system is partially fluorinated into SbClxFy (x+y=5) in the presence of HF, and the inventors found that in the case of using it as catalyst for the fluorination of compound having hydrogen or double bond capable of being chlorinated such as halogenated propene, the more the fluorine content, the more quickly the reaction of fluorinating is carried out to inhibit the formation of chlorinated product being a by-product of the reaction.

There was found that by coexistence of HF which is excessive in amount to the added antimony trihalogenide and/or antimony penta halogenide, the fluorine content of antimony trihalogenide and/or antimony pentahalogenide can be kept high and the addition reaction can be promoted to synthesize 1,1,1,3,3-pentafluoro-2-halogeno-3-chloropropane at high selectivity, having completed the third invention.

The amount of HF supplied into a reactor consists of a consumption amount of HF added by the lost amount accompanied with the product. That is, the amount of HF in the reaction system is thus kept constant. However, the variation of the range permissible in the capacity of the reactor is allowed if the excess rate of HF can be maintained. Besides, all of the required amount of HF can be also charged into the reactor before the reaction.

The introduction amount per an hour (supply rate) of halogenated propene charged into the reactor must be lesser to fluorinated-chlorinated antimony added to the system, but the lesser amount is not desirable due to decrease of the production amount per the capacity of the reactor.

But if the amount is so large, fluorine content of fluorinated-chlorinated antimony decreases so that the selectivity is lowered although the reaction proceeds. That is, the introduction amount of propene halogenide to the charged fluorinated-chlorinated antimony is usually set not more than 100 times mole/Hr and not less than 2 times mole/Hr. It is desirable to be set not more than 50 times mole/Hr and not less than 5 times mole/Hr.

The reaction advances whenever the reaction temperature is 40° C. or over, but in this case, if the supply amount of propene halogenide to the charged fluorinated-chlorinated antimony is lesser, the selectivity decreases.

A high reaction temperature is favorable in points of the productivity and the selectivity, but a reaction pressure should be kept high according to the reaction temperature. Because keeping the reaction pressure high raises the cost of equipment, the reaction is practically desirable to be carried out in the range from 50° to 150° C.

Besides, the reaction pressure is elevated according to the reaction temperature, and an adequate value can be selected in the range from 3 kg/cm$^2$ to 30 kg/cm$^2$ in order to separate HF and the product. And, the object can be obtained at high yield with keeping reaction pressure constant, by slowly supplying propene halogenide as a raw material and hydrogen fluoride into the reaction system and by selecting the produced 1,1,1,3,3-pentafluoro-2-halogeno-3-chloropropane.

Increase in amount of HF coexisted with fluorinated-chlorinated antimony in the reaction system does not affect the selectivity of the reaction, but it lowers the productivity per reactor capacity. In the case of the small amount, although the reaction advances, the supply amount of propene halogenide must be small owing to avoid the decrease of the selectivity. In practice, the reaction should be carried out in which the amount of hydrogen fluoride to fluorinated-chlorinated antimony is five times or more mole of the latter, preferably not more than five hundreds times. More desirably, HF of fifty times or over and two hundreds times or less moles is coexisted.

Still more, in addition to the above described ones, antimony trihalogenide and antimony pentahalogenide usable in the third invention are a mixture of SbF$_3$ and SbCl$_5$, SbF$_3$ with SbCl$_2$F$_3$ as a part converted by Cl$_2$ therefrom and so on.

Further, as a result of eager study by the inventors to solve the above-mentioned problems, they found that in a reaction of dehydrochlorinating of heptachloropropane, it advances under a moderate reaction condition by reacting 1,1,1,2,2,3,3-heptachloropropane with an aqueous solution of alkali metal hydroxide in the presence of a suitable phase transfer catalyst, having completed the fourth invention.

That is, the fourth invention is concerned to a method of producing 1,1,1,2,3,3-hexaohloropropene characterized in that 1,1,1,2,2,3,3-heptachloropropane is reacted with an aqueous solution of the alkali metal hydroxide in the presence of the phase transfer catalyst.

In general, an ionic compound like the alkali metal hydroxide is not soluble in heptachloropropane. Therefore, the reaction is generally carried out using a compatible solvent like alcohol. However, this method needs to separate the used reaction solvent from the produced object after the reaction. Besides, it might be considered to perform the reaction using an aqueous solution of alkali metal hydroxide in two-phase system, but the reaction is generally so slow that it often needs violent conditions in two-phase system.

However, there was found that when according to the fourth invention the reaction is carried out using the aqueous solution of alkali metal hydroxide in two-phase system under the presence of the phase transfer catalyst, particularly below-mentioned tetraalkylammonium salt or tetraalkyl phosphonium salt, it proceeds quickly in a mild condition.

For cation of tetraalkyl ammonium salt used in the reaction, benzyltriethyl ammonium, trioctylmethyl ammonium, tricaprylmethyl ammonium, and tetrabutyl ammonium etc. can be given.

And, for cation of tetraalkyl phosphonium salt, tetrabutyl phosphonium and trioctylethyl phosphonium etc. can be given.

The anion constituting the salt with the abovementioned cation is not limited, but chloride ion and hydrogensulfate ion etc. can be cited in general.

However, the above-mentioned ones are nothing but examples and does not restrict the kind of a catalyst.

Besides, for alkali metal hydroxide usable in the above-mentioned reaction, NaOH, KOH and so on can be exemplified. The concentration of the aqueous solution of this alkali metal hydroxide is not limited, however, it may be from 5 to 50%, preferably from 20 to 40% for the reaction.

These aqueous solutions can be reused after removing the produced alkali metal chloride by way of precipitation, filtration or the like and adding the alkali metal hydroxide again.

The reaction is carried out in two-phase system to generate phase separation easily so as to obtain an objective crude product of 1,1,1,2,3,3-hexachloropropene. The obtained crude product can be easily refined by distillation and the used catalyst and the unreacted heptachloropropane can be recovered.

The reaction is usually carried out at a temperature from the room temperature to 80° C., desirably from 40° to 60° C.

And, 1,1,1,2,2,3,3-heptachloropropane as a raw material can be obtained by reacting tetrachloroethylene with chloroform in the presence of a Lewis acid catalyst like alminium chloride (See Patent Opening No. 118333/1986 etc.).

Concerning from the first invention to the fourth invention as above-mentioned, the products obtained by the production method of each invention are usable as follows:

First, 1,1,1,2,3,3-hexachloropropene as a raw material which is obtained by the production method of the fourth invention can be led to 1,1,1,3,3-pentafluoro-2,3-dichloropropane by the production method of the third invention, then this can be led to 1,1,1,3,3-pentafluoropropane by the production method of the first or the second invention. The object can be obtained at high yield through this series of process from a cheap raw material easily available, which is superior in economy.

In this case, 1,1,1,2,3,3-hexachloropropene obtained by the production method of the fourth invention can be led to 1,1,1,3,3-pentafluoro-2,3-dichloropropane by the production method of the third invention, then this can be taken out as a product. In this process, there is given an advantage that the obtained product can be used as an intermediate of medicines or agricultural chemicals or an intermediate of monomer of resins.

And, 1,1,1,3,3-pentafluoro-2,3-dichloropropane as a raw material obtained by the production method of the third invention can be led to 1,1,1,3,3-pentafluoropropane by the production method of the first or second invention. This series of process brings about an advantage that 1,1,1,3,3- pentafluoropropane which is important for a urethane blowing agent can be produced at high yield.

The possibility of utilizing the invention in industry

Because in the first and second inventions the reductive reaction with hydrogen in which the raw material is 1,1,1,3,3-pentafluoro-2,3-dichloropropane is carried out in the presence of the noble metal catalyst like pallasium catalyst particularly at the temperature from 30° to 450° C., 1,1,1,3,3-pentafluoropropane can be produced at high selectivity of 80% or over.

And, the third invention can offer an industrial production method capable of manufacturing 1,1,1,3,3-pentafluoro-2-halogeno-3-chloropropane at low cost and high yield and easily because propene halogenide indicated as general formula I is fluorinated with hydrogen fluoride of mole ratio of five times or more antimony halogenide under the presence of antimony trihalogenide and/or antimony petahalogenide in a liquid phase.

Besides, in the fourth invention, 1,1,1,2,3,3-hexachloropropene can be produced at low cost in a manner that can be industrially and easily performed because of reacting 1,1,1,2,2,3,3-heptachloropropane with the aqueous solution of alkali metal hydroxide under the presence of the phase transfer catalyst.

EMBODIMENTS

Hereafter, examples of this invention will be variously explained, however, those can be variously modified on the basis of the technical concept of this invention.

EXAMPLE 1

20 cc of a palladium catalyst carried on active carbon in 0.5 % concentration was filled in a SUS316-made reaction tube having inside diameter of 2 cm and length of 40 cm and heated to 250° C. by an electric furnace under nitrogen flow. After reaching a given temperature, the nitrogen gas was replaced with hydrogen gas and this hydrogen gas was flowed for a time.

Next, beforehand gasified 1,1,1,3,3-pentafluoro-2,3-dichloropropane and hydrogen gas were introduced itno the reaction tube respectively at 16.7 cc/min and 140 cc/min. The reaction temperature was kept at 250° C.

Produced gases were analyzed by gas chromatography after washed with water and dried by calcium chloride. The result is shown in table-1.

EXAMPLE 2

A reaction was carried out under the same condition as that of Example 1 except flow rates of hydrogen gas and 1,1,1,3,3-pentafluoro-2,3-dichloropropane were respectively at 140 cc/min and 17 cc/min, and the reaction temperature was 270° C. The result is shown in table-1.

TABLE-1

| example | conversion ratio (%) | selectivity (%) |
| --- | --- | --- |
| 1 | 100 | 91 |
| 2 | 100 | 89 |

According to these results, the objective compound can be obtained at conversion ratio of 100% and high selectivity of not less than 80% by the reaction based on the first invention.

EXAMPLE 3

20 cc of a catalyst in which palladium and zirconium were carried on active carbon respectively in concentration of 0.5% and 0.25% was filled in a SUS316-made reaction tube having inside diameter of 2 cm and length of 40 cm and heated to 250° C. by an electric furnace under nitrogen flow. After reaching a predetermined temperature, the nitrogen gas was replaced with hydrogen gas and this hydrogen gas was flowed for a time.

Next, beforehand gasified 1,1,1,3,3-pentafluoro-2,3-dichloropropane and hydrogen gas were introduced into the reaction tube respectively at 16.7 cc/min and 140 cc/min. The reaction temperature was kept at 250° C.

Produced gases were analyzed by gas chromatography after washed with water and dried by calcium chloride. The result is shown in table-2.

EXAMPLE 4

A reaction was carried out under the same condition as that of Example 3 except the flow rates of hydrogen gas and 1,1,1,3,3-pentafluoro-2,3-dichloropropane were changed respectively to 120 cc/min and 35 cc/min. The result is shown in table-2.

EXAMPLE 5

20 cc of a catalyst wherein palladium and vanadium were carried on active carbon respectively in concentration of 0.5% and 0.25% was filled in a SUS316-made reaction tube having inside diameter of 2 cm and length of 40 cm and heated to 250° C. by an electric furnace under nitrogen flow. After reaching a given temperature, the nitrogen gas was changed with hydrogen gas and this hydrogen gas was flowed for a time.

Next, beforehand gasified 1,1,1,3,3-pentafluoro-2,3-dichloropropane and hydrogen gas were introduced into the reaction tube respectively at 16.7 cc/min and 140 cc/min. The reaction temperature was kept at 250° C.

Produced gases were analyzed by gas chromatography after washed with water and dried by calcium chloride. The result is shown in table-2.

EXAMPLE 6

A reaction was carried out under the same condition as that of Example 5 except changing of the flow rates of hydrogen gas and 1,1,1,3,3-pentafluoro-2,3-dichloropropane respectively to 280 cc/min and 32 cc/min. The result is shown in table-2.

TABLE-2

| example | conversion ratio (%) | selectivity (%) |
| --- | --- | --- |
| 3 | 100 | 92 |
| 4 | 100 | 89 |
| 5 | 100 | 92 |
| 6 | 100 | 88 |

According to these results, the objective compound can be obtained at conversion ratio of 100% and high selectivity of not less than 80% by the reaction based on the second invention.

EXAMPLE 7

29.9 g (0.1 mol) of $SbCl_5$ was charged into a Hastelloy-made autoclave of 500 ml with a condenser and after cooling it 300 g (15 mol) of HF was added thereto. Then, the temperature was slowly raised and the reaction was carried out at 80° C. for 3 hours.

1,1,1,2,3,3-hexachloropropene and HF were added respectively at 0.2 mol/Hr and 1.2 mol/Hr with keeping the temperature at 80° C. A reaction pressure was controlled in the range from 9 kg/cm$^2$ to 11 kg/cm$^2$ so that weight of the reactor become constant.

During the reaction, hydrogen chloride and product produced were taken out of an upper portion of the condenser, then the product was captured with a dry ice trap after hydrogen chloride was washed with water. On adding 249 g (1 mol) of 1,1,1,2,3,3-hexachloropropene, the reaction was stopped.

After the reaction, the pressure was slowly decreased and the content was selected out. As a product, 190 g of organic substance was obtained.

It was confirmed with GLC (gas-liquid chromatography) that 97% of the product was the objective 1,1,1,3,3-pentafluoro-2,3-dichloropropane (91% of the yield). A main by-product was 1,1,1,3-tetrafluoro-2,3,3-trichloropropane being a reaction intermediate and halogenated propane to which chlorine was added was not detected.

EXAMPLE 8

29.9 g (0.1 mol) of SbCl$_5$ was charged into a Hastelloy-made autoclave of 500 ml with a condenser and after cooling it 300 g (15 mol) of HF was added thereto. Then, the temperature was slowly raised and the reaction was carried out at 80° C. for 3 hours.

1,1,1,2-tetrafluoro-3,3-dichloropropene and HF were added respectively at 0.2 mol/Hr and 0.6 mol/Hr with keeping the temperature at 80° C. A reaction pressure was controlled in the range from 9 kg/cm$^2$ to 11 kg/cm$^2$.

In the reaction, hydrogen chloride and product produced were selected out of an upper portion of the condenser, then the product was collected with a dry ice trap after hydrogen chloride was washed with water. On adding 183 g (1 mol) of 1,1,1,2-tetrafluoro-3,3-dichloropropene, the reaction was stopped.

After the reaction, the pressure was slowly decreased and the content was selected out. As a product, 177 g of organic substance was obtained.

It was confirmed with GLC that 98.5% of the product was the objective 1,1,1,2,3,3-hexafluoro-3-chloropropane (94% of the yield).

A main by-product was 1,1,1,2,3-pentafluoro-3,3-dichloropropane being a reaction intermediate and halogenated propane to which chlorine was added was not detected.

EXAMPLE 9

29.9 g (0.1 mol) of SbCl$_5$ was supplied to a Hastelloy-made autoclave of 500 ml with a condenser and after cooling it 300 g (15 mol) of HF was added thereto. Then, the temperature was slowly raised and the reaction was carried out at 80° C. for 3 hours.

1,1,1-trifluoro-2,3,3-trichloropropene and HF were added respectively at 0.2 mol/Hr and 0.8 mol/Hr with keeping the temperature at 80° C. A reaction pressure was controlled in the range from 10 kg/cm$^2$ to 12 kg/cm$^2$.

In the reaction, hydrogen chloride and product produced were selected out of an upper portion of the condenser, then the product was captured with a dry ice trap after hydrogen chloride was washed with water. On adding 199 g (1 mol) of 1,1,1-trifluoro-2,3,3-trichloropropene, the reaction was stopped.

After the reaction, the pressure was slowly decreased the content was selected out. As a product, 198 g of organic substance was obtained.

It was confirmed with GLC that 98% of the product was the objective 1,1,1,3,3-pentafluroro-2,3-dichloropropane (96% of the yield).

A main by-product was 1,1,1,3-tetrafluoro-2,3,3-trichloropropane being a reaction intermediate and halogenated propane to which chlorine was added was not detected.

EXAMPLE 10

A reaction was carried out under the same condition as that of Example 7 except charging 29.9 g (0.1 mol) of SbCl$_5$ and 17.9 g (0.1 mol) of SbF$_3$ in a Hastelloy-made autoclave of 500 ml with a condenser.

as a product, 196 g of organic substance was obtained. It was confirmed with GLC that 98% of the product was the objective 1,1,1,3,3-pentafluroro-2,3-dichloropropane (94% of the yield). A main by-product was 1,1,1-tetrafluoro-2,3,3-trichloropropane and a compound with added chlorine was not detected.

According to the above-mentioned results, by the reaction based on the third invention 1,1,1,3,3-pentafluoro-2-halogeno-3-chloropropane can be produced easily at high yield.

EXAMPLE 11

285.5 g (1.0 mol) of 1,1,1,2,2,3,3-heptachloropropane and 0.3 g (0.1 mmol) of tetrabutyl ammonium chloride were charged into a round bottom flask of 500 ml with a Dimroth condenser and a dropping funnel.

With keeping it at 40° C. and agitating violently, 250 ml of KOH aqueous solution of 20% concentration was dropped for 1 hour. After the dropping was finished, the agitating was stopped and an organic layer or a lower layer was analyzed. 1,1,1,2,2,3,3-heptachloropropane as a raw material disappeared and the organic layer consisted of only 1,1,1,2,3,3-hexaohloropropene.

The reaction solution was transferred to a separatory funnel to separate the organic layer. After washing with a saturated salt solution two times, it was dried with magnesium sulfate to obtain 237 g (95%) of crude 1,1,1,2,3,3-hexachloropropene.

EXAMPLE 12

285.5 g (1.0 mol) of 1,1,1,2,2,3,3-heptachloropropane and 0.3 g (0.1 mmol) of tricaprylmethyl ammonium chloride were supplied to a round bottom flask of 500 ml with a Dimroth condenser and a dropping funnel.

With keeping it at 40° C. and agitating violently, 250 ml of KOH aqueous solution of 20% concentration was dropped for 1 hour. After the dropping was finished, the reaction was carried out for 1 hour. Then,the agitating was stopped and a lower organic layer was analyzed. 1,1,1,2,2,3,3-heptachloropropane as a raw material disappeared and the organic layer consisted of only 1,1,1,2,3,3-hexachloropropene.

The reaction solution was transferred to a separatory funnel to separate the organic layer. After washing with a saturated salt solution two times, it was dried with magnesium sulfate to obtain 232 g (93%) of crude 1,1,2,3,3-hexaohloropropene.

EXAMPLE 13

285.5 g (1.0 mol) of 1,1,1,2,2,3,3-heptachloropropane and 0.3 g (0.1 mmol) of tetrabutyl phosphonium chloride were charged into a round bottom flask of 500 ml with a Dimroth condenser and a dropping funnel.

With keeping it at 40° C. and agitating violently, 250 ml of KOH aqueous solution of 20% concentration was dropped for 1 hour. After the dropping was finished, the agitating was stopped and a lower organic layer was analyzed. 1,1,1,2,2,3,3-heptachloropropane as a raw material disappeared and the organic layer consisted of only 1,1,1,2,3,3-hexachloropropene.

The reaction solution was transferred to a separatory funnel to separate the organic layer. After washing with a saturated salt solution two times, it was dried with magnesium sulfate to obtain 239 g (96%) of crude 1,1,1,2,3,3-hexachloropropene.

EXAMPLE 14

285.5 g (1.0 mol) of 1,1,1,2,2,3,3-heptachloropropane and 0.3 g (0.1 mmol) of trioctylmethyl ammonium chloride were charged into a round bottom flask of 500 ml with a Dimroth condenser and a dropping funnel.

With keeping it at 40° C. and agitating violently, 250 ml of KOH aqueous solution of 20% concentration was dropped for 1 hour. After the dropping was finished, a reaction was advanced for 2 hours. Then the agitating was stopped and a lower organic layer was analyzed. 1,1,1,2,2,3,3-heptachloropropane as a raw material disappeared and the organic layer consisted of only 1,1,1,2,3,3-hexachloropropene.

The reaction solution was transferred to a separatory funnel to separate the organic layer. After washing with a saturated salt solution two times, it was dried with magnesium sulfate to obtain 237 g (95%) of crude 1,1,1,2,3,3-hexachloropropene.

Comparative example 1

285.5 g (1.0 mol) of 1,1,1,2,2,3,3-heptachloropropane was charged into a round bottom flask of 500 ml with a Dimroth condenser and a dropping funnel.

With keeping it at 40° C. and agitating violently, 250 ml of KOH aqueous solution of 20% concentration was dropped for 1 hour. After the dropping was finished, a reaction was carried out for 3 hours. Then, the agitating was stopped and a lower organic layer was analyzed.

The reaction was carried out only a little, 63% of the organic layer consisted of 1,1,1,2,2,3,3-heptachloropropane a as a raw material, and the conversion ratio was 37%.

According to the above-mentioned results, 1,1,1,2,3,3-hexachloropropene can be easily produced by the reaction based on the fourth invention.

EXAMPLE 15

By reacting under the same condition as that of Example 11 except for the alkali aqueous solution used therein 20% KOH aqueous solution was changed with 20% NaOH aqueous solution, 232 g (93%) of crude 1,1,1,2,3,3-hexachloropropene was obtained.

EXAMPLE 16

A reaction was carried out under the same condition as that of Example 7 except charging 29.9 g (0.1 mol) of $SbCl_5$ and 22.9 g (0.1 mol) of $SbCl_3$ into a Hastelloy-made autoclave of 500 ml with a condenser.

As a product, 194 g of organic substance was obtained. It was confirmed with GLC that 98% of the product was the objective 1,1,1,3,3-pentafluroro-2,3-dichloropropane (93% of the yield). A main by-product was 1,1,1-tetrafluoro-2,3,3-trichloropropane and a compound added by chlorine was not detected.

What is claimed is:

1. A method of producing 1,1,1,3,3-pentafluoropropane which comprises reacting gaseous 1,1,1,3,3-pentafluoro-2,3-dichloropropane with hydrogen in the presence of a noble metal catalyst.

2. The method according to claim 1, wherein the noble metal is palladium.

3. A method according to claim 2, wherein the catalyst contains at least one of vanadium or zirconium.

4. A method according to claim 3, wherein the catalyst contains vanadium.

5. A method according to claim 1, wherein the catalyst is supported on a carrier.

6. A method according to claim 5, wherein the carrier is active carbon, silica gel, titanium oxide or zirconia.

7. A method according to claim 6, wherein 0.05 to 10% by weight of the catalyst is support on the carrier.

8. A method according to claim 1, wherein at least a stoichiometric amount of hydrogen is reacted with 1,1,1,3,3-pentafluoro-2,3-dichloropropane.

9. A method according to claim 8, wherein hydrogen is reacted with 1,1,1,3,3-pentafluoro-2,3-dichloropropane at a temperature of from 30° to 450° C.

10. A method of producing 1,1,1,3,3-pentafluoropropane which comprises reacting 1,1,1,2,2,3,3-heptachloropropane with an alkali metal hydroxide in the presence of a phase transfer catalyst to form 1,1,1,2,3,3-hexachloropropene; continuously reacting, at a constant pressure and in the liquid phase, 1,1,1,2,3,3-hexachloropropene with excess hydrogen fluoride in the presence of at least one of an antimony trihalogenide and an antimony pentahologenide while selectively removing 1,1,1,3,3-pentafluoro-2,3-dichloropropane as it is formed; and reacting gaseous 1,1,1,3,3-pentafluoro-2,3-dichloropropane with hydrogen in the presence of a noble metal catalyst.

* * * * *